(12) United States Patent
Saptari (10) Patent No.: US 9,488,570 B2
(45) Date of Patent: Nov. 8, 2016

(54) SYSTEMS AND METHODS FOR PRESSURE DIFFERENTIAL MOLECULAR SPECTROSCOPY OF COMPRESSIBLE FLUIDS

(71) Applicants: MKS Instruments, Inc., Andover, MA (US); Pason Systems Corp., Calgary, Alberta (CA)

(72) Inventor: Vidi A. Saptari, Lexington, MA (US)

(73) Assignees: Pason Systems Corp., Calgary (CA); MKS Instruments, Inc., Andover, MA (US)

( * ) Notice: Subject to any disclaimer, the term of this patent is extended or adjusted under 35 U.S.C. 154(b) by 69 days.

(21) Appl. No.: 14/511,842

(22) Filed: Oct. 10, 2014

(65) Prior Publication Data

US 2015/0131093 A1 May 14, 2015

Related U.S. Application Data

(60) Provisional application No. 61/890,119, filed on Oct. 11, 2013.

(51) Int. Cl.
*G01N 21/31* (2006.01)
*G01N 21/05* (2006.01)
*G01N 21/3504* (2014.01)
(Continued)

(52) U.S. Cl.
CPC ........... *G01N 21/31* (2013.01); *G01N 21/05* (2013.01); *G01N 21/3504* (2013.01); *G01N 21/359* (2013.01); *G01N 21/3518* (2013.01);
(Continued)

(58) Field of Classification Search
CPC . G01N 21/31; G01N 21/05; G01N 2201/023

USPC ................. 356/432–437, 440, 246, 39, 326; 436/126, 164, 171; 600/309
See application file for complete search history.

(56) References Cited

U.S. PATENT DOCUMENTS 3,836,255 A * 9/1974 Schuman ............... G01N 21/71
250/343
4,500,207 A 2/1985 Maiden
(Continued)

FOREIGN PATENT DOCUMENTS

EP 1203942 A1 5/2002

OTHER PUBLICATIONS

International Search Report for PCT/US2014/060071, 3 pages (Dec. 1, 2014).
(Continued)

*Primary Examiner* — Sang Nguyen
(74) *Attorney, Agent, or Firm* — Choate, Hall & Stewart—LLP; William R. Haulbrook; Margo R. Monroe (57) ABSTRACT

Described herein is a spectroscopic system and method for measuring and monitoring the chemical composition and/or impurity content of a sample or sample stream using absorption light spectroscopy. Specifically, in certain embodiments, this invention relates to the use of sample pressure variation to alter the magnitude of the absorption spectrum (e.g., wavelength-dependent signal) received for the sample, thereby obviating the need for a reference or 'zero' sample. Rather than use a reference or 'zero' sample, embodiments described herein obtain a spectrum/signal from a sample-containing cell at both a first pressure and a second (different) pressure.

5 Claims, 5 Drawing Sheets

Spectroscopic system, including electromagnetic radiation source, optics for directing electromagnetic radiation source through the cell, optical detector array, processor, and memory (51) Int. Cl.
*G01N 33/22* (2006.01)
*G01N 21/359* (2014.01)
*G01N 21/3518* (2014.01)

(52) U.S. Cl.
CPC ..... *G01N33/225* (2013.01); *G01N 2021/3536* (2013.01); *G01N 2201/023* (2013.01)

(56) References Cited

U.S. PATENT DOCUMENTS

| | | | | |
|---|---|---|---|---|
| 5,371,019 A | * | 12/1994 | Manz | G01N 33/0016 422/82.05 |
| 5,514,595 A | * | 5/1996 | Olds | G01N 1/42 422/82.09 |
| 5,906,106 A | * | 5/1999 | Brown | F25B 43/04 62/126 |
| 6,474,152 B1 | | 11/2002 | Mullins et al. | |
| 2005/0036146 A1 | * | 2/2005 | Braig | G01N 21/03 356/436 |
| 2010/0027004 A1 | * | 2/2010 | Bonyuet | G01J 3/02 356/326 |
| 2011/0211193 A1 | | 9/2011 | Saveliev et al. | |
| 2012/0065482 A1 | * | 3/2012 | Robinson | A61B 5/14532 600/309 |

OTHER PUBLICATIONS

Written Opinion for PCT/US2014/060071, 7 pages (Dec. 1, 2014).

* cited by examiner

SYSTEMS AND METHODS FOR PRESSURE DIFFERENTIAL MOLECULAR SPECTROSCOPY OF COMPRESSIBLE FLUIDS

PRIORITY

This application claims priority to and the benefit of U.S. Provisional Patent Application No. 61/890,119, filed Oct. 11, 2013, titled "Systems and Methods for Pressure Differential Molecular Spectroscopy of Compressible Fluids," the content of which is incorporated by reference herein in its entirety.

TECHNICAL FIELD

This invention relates generally to spectroscopic systems and related methods for identifying the chemical composition of compressible fluids.

BACKGROUND

Spectroscopy refers to the study and measurement of light interaction with matter as a function of wavelength. A spectroscopic device generally includes a light source, a wavelength separating or scanning module, a sample cell, and a light detector. Absorption spectroscopy is a technique for identifying the chemical composition of a sample by measuring the absorption of light (or other electromagnetic radiation) passing through the sample as a function of wavelength (or frequency). Absorption spectroscopy is an inherently relative method in that it involves obtaining a spectrum (e.g., a wavelength-dependent signal) of a given sample as well as the spectrum of a known reference, then determining the ratio, difference, or other comparison of the reference spectrum and sample spectrum. In gas phase infrared measurement, the reference or zero beam is often acquired with nitrogen in the sample cell, because nitrogen is an inert gas that does not have any infrared absorption. Depending on the application, another reference or zero gas may be used such as air, argon, helium, etc. A sample spectrum (e.g., signal determined over a range of wavelengths, or at a given set of discrete wavelengths) is acquired with the sample cell filled with the sample being measured. The absorption spectrum can then be computed as the ratio of the sample beam and the zero beam. Generally, the logarithm of the ratio is used to provide linearization of the absorption signal with respect to the density of the molecules or the concentration.

Providing an acceptable reference or zero sample can be problematic due to various technical and/or practical reasons. For example, in the case of a high-purity trace monitoring application, the reference or 'zero' needs to be orders of magnitude purer than the target detection limit of the measurement—this may not be commercially or practically available. In other cases, such as in remote stand-alone deployment, maintenance and support for such reference sample is difficult.

Thus, there is a need for spectroscopic systems and methods that address these practical limitations.

SUMMARY OF THE INVENTION

Described herein is a spectroscopic system and method for measuring and monitoring the chemical composition and/or impurity content of a sample or sample stream using absorption light spectroscopy. Specifically, in certain embodiments, this invention relates to the use of sample pressure variation to alter the magnitude of the absorption spectrum (e.g., wavelength-dependent signal) received for the sample, thereby obviating the need for a reference or 'zero' sample. Rather than using a reference or 'zero' sample, embodiments described herein obtain a spectrum/signal from a sample-containing cell at both a first pressure and a second (different) pressure.

Where the sample is a compressible fluid (e.g., gas), the molecular density of the sample in the cell is varied by changing the pressure, thus creating a differential absorption spectrum/signal. It is found that this differential allows for accurate normalization of a sample signal without use of a reference sample of different composition than the sample. For industrial settings, in particular, where intermittent, continuous, or semi-continuous monitoring of a sample stream (e.g., for the presence of an impurity) is necessary, it is very desirable to eliminate the need for maintaining a sufficiently pure reference (zero) sample.

Embodiments described herein are applicable for measurement of compressible liquids, vapors and gases with a variety of spectroscopic instrumentations types. For example, the pressure differential technique described herein may be employed with various types of spectrometer hardware and software, for example, a Fourier transform infrared spectrometer (FTIR), a dispersive spectrometer (spectrograph or monochromator), and/or a non-dispersive or filter-based spectrometer.

In one aspect, the invention is directed to a spectroscopic system for measuring chemical composition and/or trace impurities in a compressible fluid sample, the system comprising: an electromagnetic radiation source for generating electromagnetic radiation (e.g., light); optics for directing the generated electromagnetic radiation (e.g., filtered or unfiltered) through a sample cell containing a compressible fluid sample (e.g., a gas or compressible liquid); an optical detector array for receiving electromagnetic radiation from the sample cell containing the fluid sample and for generating an electrical signal indicative of spectral information associated with the fluid sample (e.g., a spectrum); a pressure modulating system for varying the pressure of the fluid sample in the sample cell, thereby varying sample density; and a processor and memory having instructions stored thereon, wherein the instructions, when executed by the processor, cause the processor to identify and/or analyze at least two absorption spectra obtained at different sample pressures (e.g., but with the same sample composition), thereby identifying a differential absorption spectrum for the sample, (e.g., and to perform spectral decomposition and compound speciation, thereby identifying one or more constituents of the sample, and/or identifying a concentration of one or more of the one or more constituents of the sample).

In certain embodiments, the pressure modulating system comprises: a valve assembly having a first input port, a second input port, and an output port, the valve assembly being configured to selectably permit flow (i) between the first input port and the output port and (ii) between the second input port and the output port, according to a selectable configuration of the valve assembly; and a check valve connecting between the first input port and the second input port to allow setting of measurement pressure of the fluid sample in the sample cell. In certain embodiments, the valve assembly comprises a three-way valve (e.g., solenoid valve) (e.g., or equivalents, such as two or more two-way valves).

In certain embodiments, the sample cell is a flow cell permitting flow of the sample therethrough during measurement (e.g., allowing continuous, semi-continuous, or intermittent monitoring of chemical composition and/or trace impurity detection of a flowing sample, e.g., in an industrial gas line).

In certain embodiments, the pressure modulating system allows for setting measurement pressure of the fluid sample in the sample cell at a first pressure and at a second pressure while maintaining a consistent flow rate throughout measurement.

In another aspect, the invention is directed to a method for measuring chemical composition and/or trace impurities in a compressible fluid sample without the need for a 'zero' reference (e.g., where the 'zero' reference has a different composition than the sample), the method comprising: obtaining a first spectrum for a sample cell containing a sample fluid (e.g., a gas or compressible liquid) from a spectroscopic system with the sample fluid at a first pressure in the sample cell; obtaining a second spectrum for the sample cell containing the sample fluid from the spectroscopic system with the sample fluid at a second pressure in the sample cell, wherein the first pressure is different from the second pressure; determining a differential absorption spectrum for the sample using the first spectrum and the second spectrum; and identifying one or more constituents of the sample, and/or identifying a concentration of one or more of the one or more constituents of the sample, using the differential absorption spectrum.

In certain embodiments, the sample cell is a flow cell and the sample is drawn from a compressible fluid line (e.g., where the compressible fluid flows through the fluid line continuously, semi-continuously, and/or intermittently).

In certain embodiments, the compressible fluid line is a natural gas pipeline stream and wherein the one or more constituents of the sample that are identified comprises one or more members selected from the group consisting of $CH_4$, $C_2H_6$, $C_3H_8$, $i\text{-}C_4H_{10}$, $n\text{-}C_4H_{10}$, $C_5H_{12}$, and $CO_2$.

In certain embodiments, the compressible fluid line is an LNG line and wherein the one or more constituents of the sample that are identified comprises one or more members selected from the group consisting of $CH_4$, $C_2H_6$, $C_3H_8$, $i\text{-}C_4H_{10}$, $n\text{-}C_4H_{10}$, and $C_5H_{12}$.

In certain embodiments, the compressible fluid line is an LPG line and wherein the one or more constituents of the sample that are identified comprises one or more members selected from the group consisting of $C_2H_6$, $C_3H_8$, $i\text{-}C_4H_{10}$, $n\text{-}C_4H_{10}$, and $C_5H_{12}$.

In certain embodiments, the compressible fluid line is an acid and/or sour gas line and wherein the one or more constituents of the sample that are identified comprises one or more members selected from the group consisting of $H_2S$, $CH_4$, $C_2H_6$, $C_3H_8$, $i\text{-}C_4H_{10}$, $n\text{-}C_4H_{10}$, $C_5H_{12}$, $CO_2$, $NH_3$, and $H_2O$.

In certain embodiments, the compressible fluid line is a biomethane, syngas, and/or waste gas line and wherein the one or more constituents of the sample that are identified comprises one or more members selected from the group consisting of CO, $CO_2$, $CH_4$, $H_2S$, and $H_2O$.

In certain embodiments, the compressible fluid line is an olefins line and the one or more constituents of the sample that are identified comprises one or more members selected from the group consisting of $CH_4$, $C_2H_6$, $C_2H_4$, $C_3H_8$, $C_3H_6$, $i\text{-}C_4H_{10}$, $n\text{-}C_4H_{10}$, an alkane, an alkyne, an alkene, CO, $CO_2$, $H_2S$, $H_2$, and $O_2$.

In certain embodiments, the compressible fluid line is a flare stack gas line and the one or more constituents of the sample that are identified comprises a C1-C6 alkane.

In certain embodiments, the first pressure is 0 psig. In certain embodiments, the first pressure and the second pressure differ by no less than 5 psig. In certain embodiments, the first pressure and the second pressure differ by no less than 10 psig.

Elements of embodiments described with respect to a given aspect of the invention may be used in various embodiments of another aspect of the invention. For example, it is contemplated that features of dependent claims depending from one independent claim can be used in systems and/or methods of any of the other independent claims.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

In some embodiments, the system for measuring chemical composition and/or trace impurities in a compressible fluid sample includes a broadband light source, a wavelength scanning or separating element, a sample cell, a detection element or system, a pressure modulation device or system, and control and signal processing electronics. The pressure modulation or varying system may include, for example, a pump and an electronic back pressure regulator, connected to the control electronics with the proper software logic.

Embodiments described herein employ a sample pressure differential method for absorption spectroscopy, providing the ability to perform absorption spectroscopic measurement without the need for a reference or zero sample. Embodiments are applicable to measurements of compressible liquids, vapors and gases with a variety of spectroscopic instrumentations types. The reference single beam or signal is obtained with the sample cell filled with the sample at a certain pressure, while the sample beam or signal is obtained with the cell filled with the same sample at a different pressure. By varying the pressure, the molecular density of the sample in the cell is varied, thus creating a differential absorption signal or spectrum.

Figure 1:
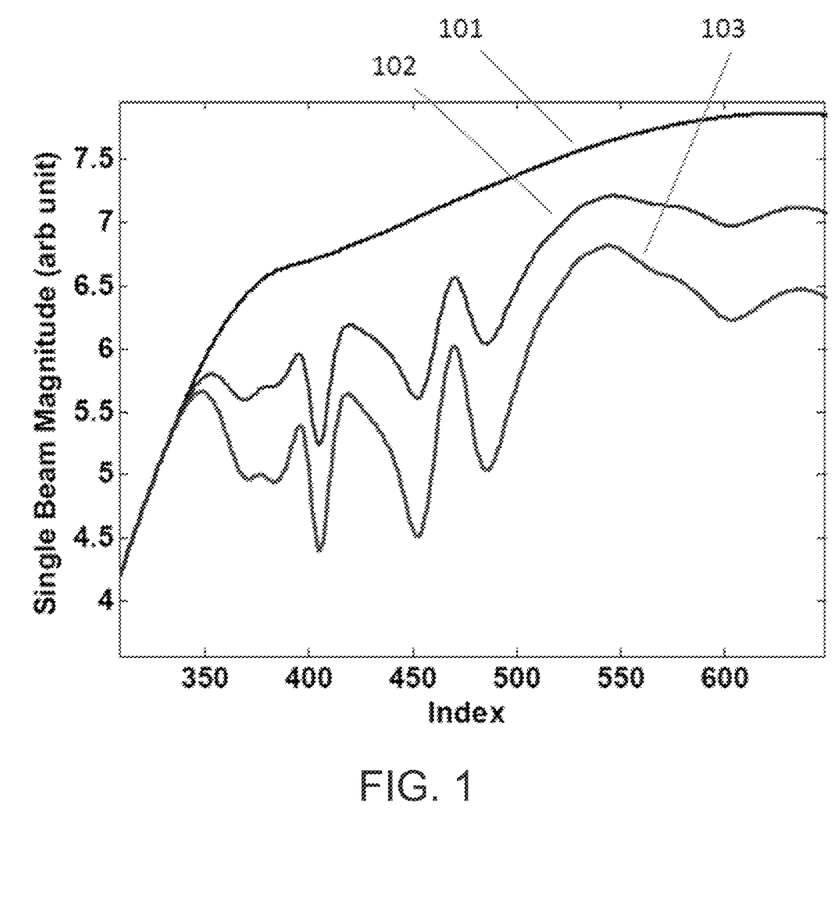
FIG. 1 is a plot of an absorption spectrum of a 'zero' reference sample (nitrogen), along with the absorption spectrum of a methane sample at two different pressures.
Figure 2:
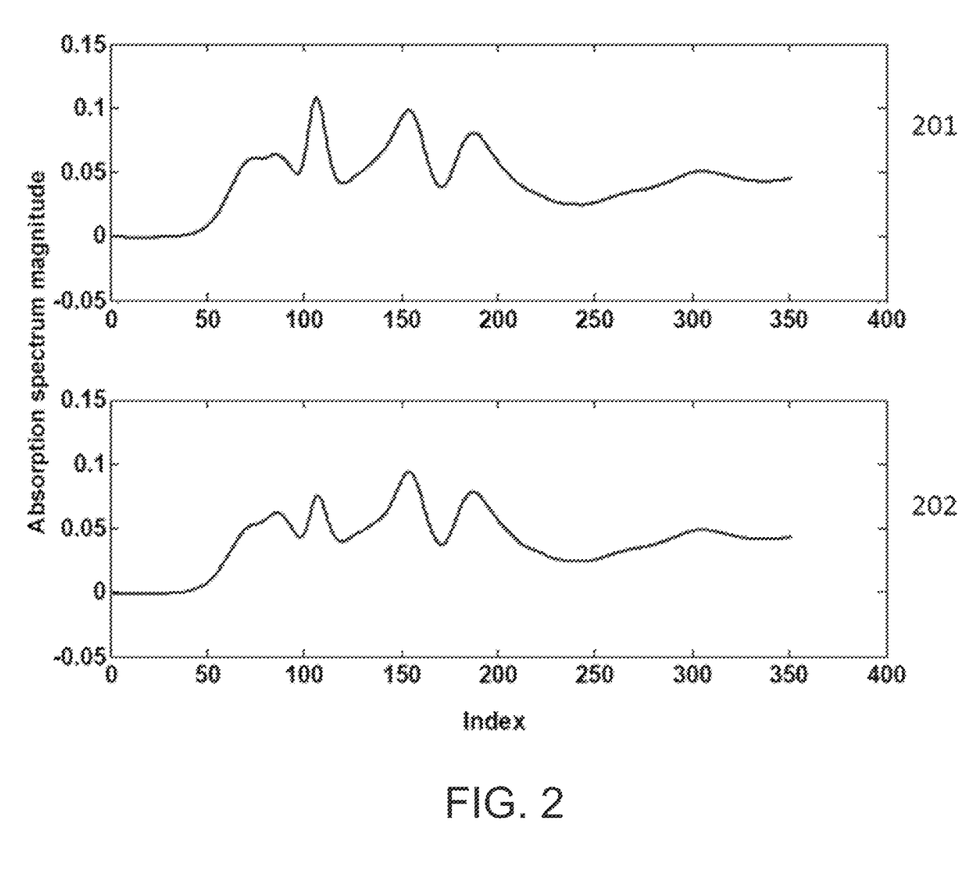
FIG. 2 is a plot of the methane sample from FIG. 1 that was obtained at a first pressure (0 psig) normalized using the nitrogen reference sample spectrum (top plot), and normalized using the spectrum of the methane sample obtained at a second pressure (15 psig) (bottom plot), according to an illustrative embodiment of the invention.

An example is illustrated for the case of absorption spectroscopy measurement of methane in the near infrared. FIG. 1 shows a single beam spectrum of nitrogen (101) which generally serves as the reference or zero beam, a single beam spectrum of 100% methane at 0 psig (102) and a single beam spectrum of 100% methane at 15 psig (103). FIG. 2 shows the absorption spectrum of the methane sample at 0 psig referenced to the nitrogen gas (201) and the absorption spectrum of the methane sample at 15 psig referenced to the same methane sample (same 100% concentration) at 0 psig (202). As seen in FIG. 2, the second spectrum 202 provides comparable details and magnitude as the first spectrum 201, such that it can be used to provide quantitative information of the sample through proper spectral processing, as the first spectrum. By doing that, no separate reference gas, in this particular example, nitrogen, is needed.

Figure 3:
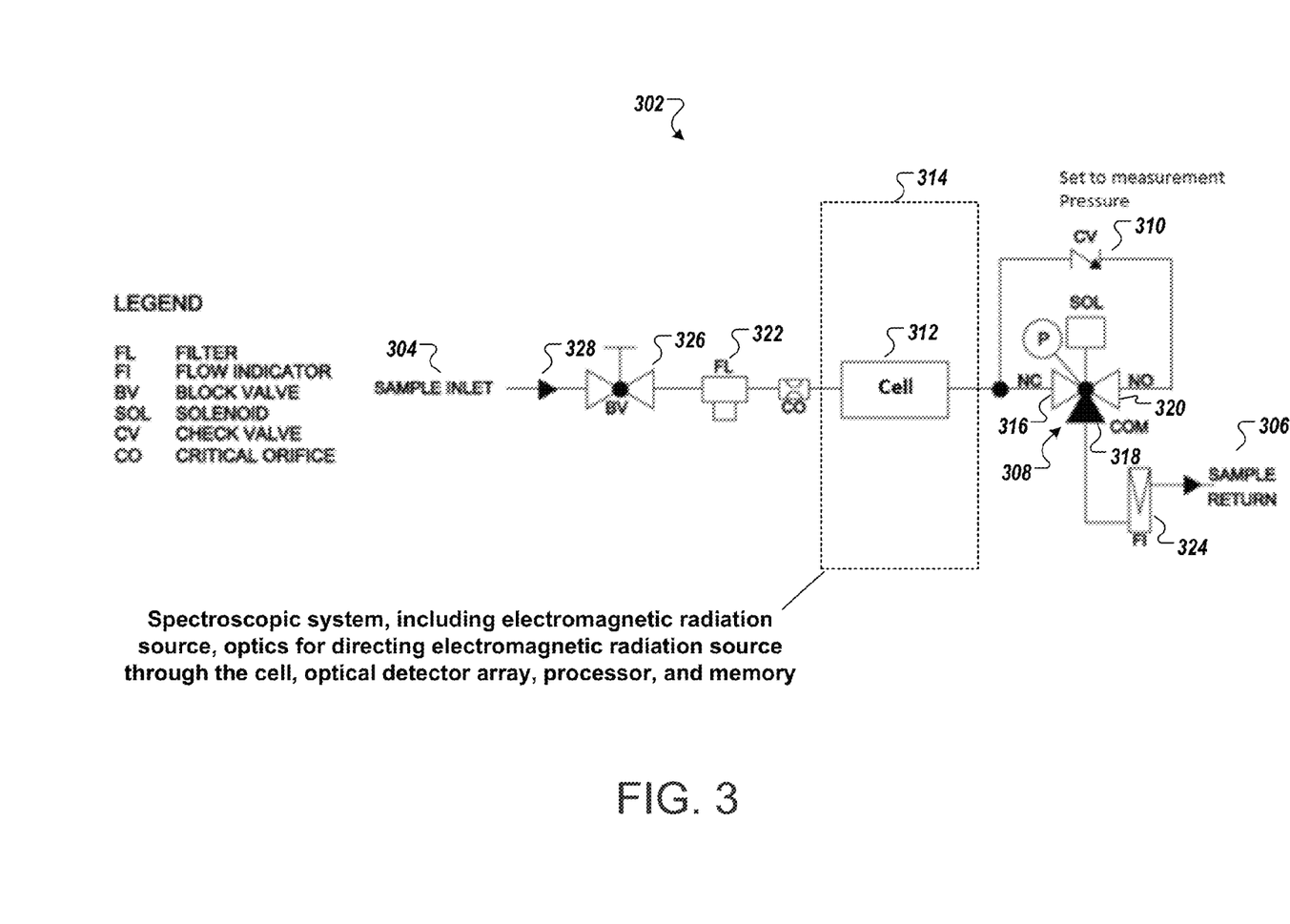
FIG. 3 is a schematic drawing of a pneumatic implementation of a sampling system for obtaining spectra at two different pressures, according to an illustrative embodiment of the invention.

An example of a pneumatic implementation for the spectroscopic system 302 is shown in FIG. 3. This implementation allows for the setting of two levels of sample pressure while maintaining consistent flow rate and without the use of complicated control electronics and electro-mechanical elements. With this arrangement, the sample inlet 304 is assumed to be at a certain higher pressure range than the sample return 306 such that no sample pump is needed. A simple 3-way solenoid valve 308 ("SOL") is used to switch between the high-pressure measurement and the low-pressure zeroing. A check valve 310 ("CV") is used to set the pressure for measurement, and the sample return line 306 inherently set the pressure for zeroing. In certain embodiments, the cell 312 (e.g., flow cell) shown in FIG. 3 is part of a spectroscopic system 314 which includes an electromagnetic radiation source, optics for directing electromagnetic radiation through the cell, an optical detector array, a processor, and memory for recording the spectra obtained at the different pressures and determining the chemical composition and/or identifying the trace impurity(ies).

As shown in FIG. 3, the 3-way solenoid valve 308 is a part of a pressure modulating system. The 3-way solenoid valve 308 varies the pressure of the fluid sample in the sample cell 312 by selectably permitting flow i) between a first input port 316 and an output port 318 and ii) between a second input port 320 and the output port 318. The first input port 316, in some embodiments, is a "normally-closed" value and the second input port 320 is a "normally-opened" value. The pneumatic implementation of the spectroscopic system 302, in some embodiments, includes one or more filters 322, flow indicators 324, block valves 326, and check valves 328.

In certain embodiments, the pressure modulation is automatically controlled, varying between two or more pressure magnitudes, as a function of time. For example, spectra may be obtained periodically, e.g., every 24 hours, every hour, or at any other interval of time, for a fluid sample at two different pressures.

The pressure modulation frequency can be based on certain spectral characteristics indicative of instrumental drifts, environmental drifts, presence of contaminants, and other conditions that would require a "re-zero" or re-establishment of baseline.

In certain embodiments, a method is provided that measures chemical composition and/or trace impurities in a compressible fluid sample without the need for a 'zero' reference having a composition different from the compressible fluid sample being measured. A first spectrum is obtained from the spectroscopic system for the sample at a first pressure in the sample cell. Then, a second spectrum is obtained for the sample at a second pressure different from the first pressure. A differential absorption spectrum (e.g., a normalized spectrum, or other calculation) is then obtained for the sample using the first spectrum and the second spectrum. One or more constituents of the sample are then identified using the differential absorption spectrum (e.g., via known spectral decomposition and compound speciation techniques), and a concentration of one or more of the one or more constituents of the sample is determined using the differential absorption spectrum.

Assuming a linear relationship between the magnitude of the absorption spectra and the pressure, Equations 1 and 2 may be used to compute the predicted concentration values $c_{pred}$:

$$c_{pred} = (c_{zero} + c_{raw})/P \quad (1)$$

$$c_{zero} = c_0/(P - P_{zero}) \quad (2)$$

where $c_0$ is the predicted concentration of the zero sample at the measurement pressure, e.g., the first predicted concentration at the time of collection of the zero spectrum; $c_{raw}$ is the raw predicted concentration value deduced from the absorption spectrum magnitude of the sample at measurement pressure referenced to the spectrum at zero pressure (0 psig); P is the measurement pressure; and $P_{zero}$ is the zero pressure (e.g., 0 psig).

The methods and systems described herein can be used for the measurement (detection and/or concentration determination) of hydrocarbons in a compressible fluid state, for example, substituted and unsubstituted C1-C6 hydrocarbons such as methane, ethane, ethene, chloroethane, tetrafluoroethane, propane, propene, cyclopropane, butane, cyclobutane, butene, pentane, pentene, cyclopentane, hexane, cyclohexane, cyclohexene, and benzene, as well as substituted and unsubstituted C7 and higher hydrocarbons. The methods and systems can also be used, for example, for trace detection of CO, $CO_2$, and/or $H_2O$ in hydrocarbon samples/streams. In general, the methods and systems can be used for compressible fluids which have an absorption spectrum that increases in intensity as a result of increasing pressure.

In some embodiments, measurement is performed for a natural gas pipeline stream, for example, for measurement of $CH_4$, $C_2H_6$, $C_3H_8$, i-$C_4H_{10}$, n-$C_4H_{10}$, $C_5H_{12}$, and/or $CO_2$. In some embodiments, measurement is performed for an LNG line, for example, for measurement of $CH_4$, $C_2H_6$, $C_3H_8$, i-$C_4H_{10}$, n-$C_4H_{10}$, and/or $C_5H_{12}$. In some embodiments, measurement is performed for an LPG line, for example, for measurement of $C_2H_6$, $C_3H_8$, i-$C_4H_{10}$, n-$C_4H_{10}$, and/or $C_5H_{12}$. In some embodiments, measurement is performed for an acid & sour gas line, for example, for measurement of $H_2S$, $CH_4$, $C_2H_6$, $C_3H_8$, i-$C_4H_{10}$, n-$C_4H_{10}$, $C_5H_{12}$, $CO_2$, $NH_3$, and/or $H_2O$. In some embodiments, measurement is performed for a biomethane, syngas, and/or waste gas line, for example, for measurement of CO, $CO_2$, $CH_4$, $H_2S$, and/or $H_2O$. In some embodiments, measurement is performed for an olefins line, for example, for measurement of $CH_4$, $C_2H_6$, $C_2H_4$, $C_3H_8$, $C_3H_6$, i-$C_4H_{10}$, n-$C_4H_{10}$, alkanes, alkynes, alkenes, CO, $CO_2$, $H_2S$, $H_2$, and/or $O_2$. In some embodiments, measurement is performed for a flare stack gas line, for example, for measurement of methane through n-hexane.

In some embodiments, a spectrum for a sample is obtained at a first pressure, where the first pressure is 0 psig. Another spectrum is obtained for the sample at a second pressure higher than the first pressure, for example, 5 psig or higher (e.g., ≥5 psig, ≥10 psig, ≥15 psig, ≥25 psig, ≥40 psig, ≥50 psig, ≥100 psig). The second pressure used is one which shows a change in the absorption spectrum. In some embodiments, the second pressure is limited by the pressure available from the sample line. For example, in a line with 8 psig of pressure available, the second pressure may be chosen as 8 psig. Much higher pressures can be used as well, for example, even thousands of psig—the limitation in such cases may be the mechanical integrity of the sample cell (to withstand the high pressure).

Measurements may be obtained at more than two different pressures, for example, to improve accuracy of the concentration/detection determination.

In some embodiments, a tunable filter spectrometer is used, for example, where obtained spectra may range from UV (ultraviolet) to IR (infrared) spectral regions. The wavelength ranges covered by the obtained spectra depend on the compounds being detected, as understood by one of skill in the art. An example spectrometer that can be used includes the system described in U.S. Pat. No. 8,184,293, issued May 22, 2012 entitled, "Methods and Systems for Chemical Composition Measurement and Monitoring Using a Rotating Filter Spectrometer," which is incorporated herein by reference. Other spectrometers can also be used.

Figure 4:
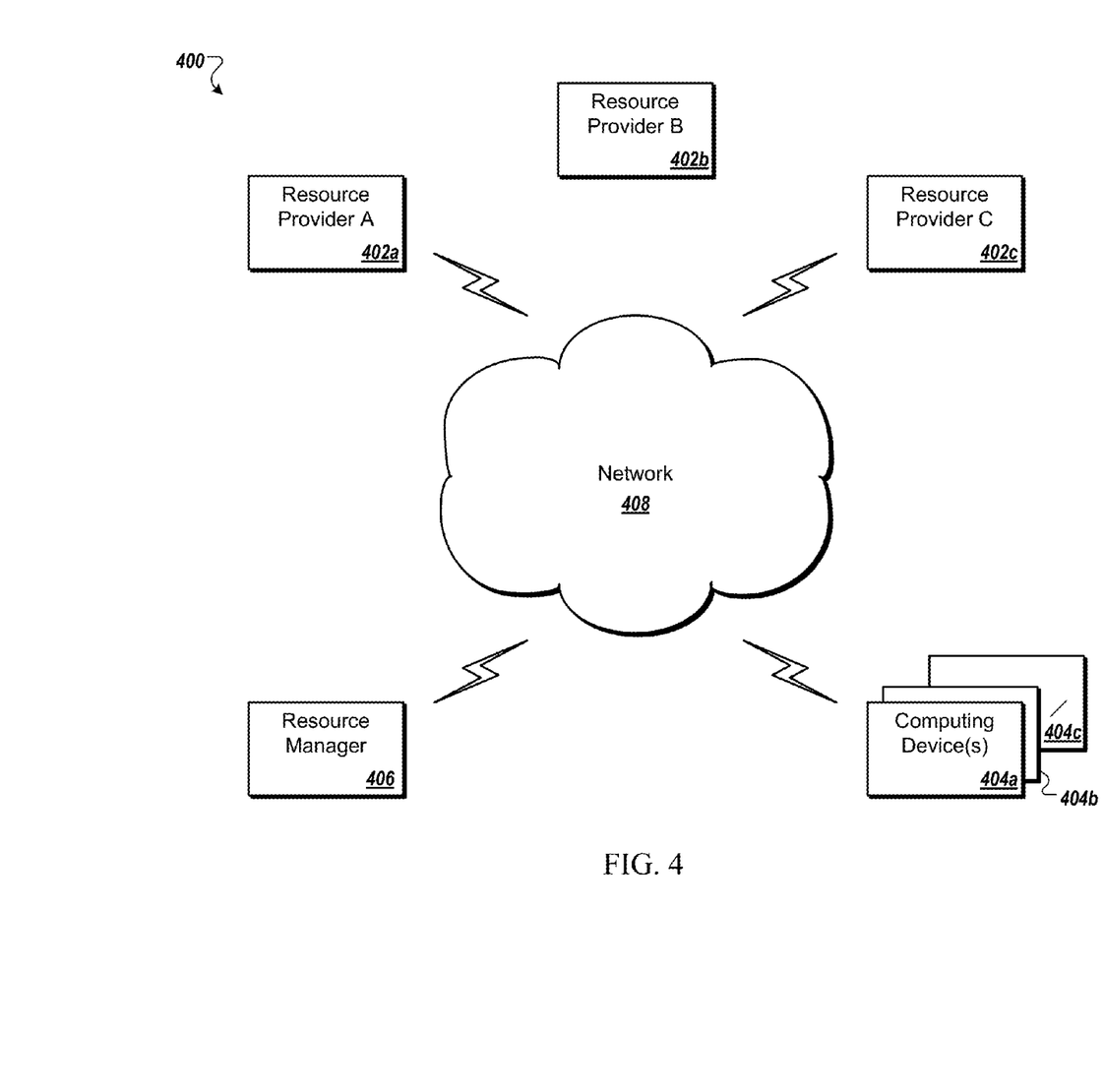
FIG. 4 is a block diagram of an example computer network environment for use in illustrative embodiments described herein.

FIG. 4 shows an illustrative network environment 400 for use in the methods and systems described herein. In brief overview, referring now to FIG. 4, a block diagram of an exemplary cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 102 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 1302 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

Figure 5:
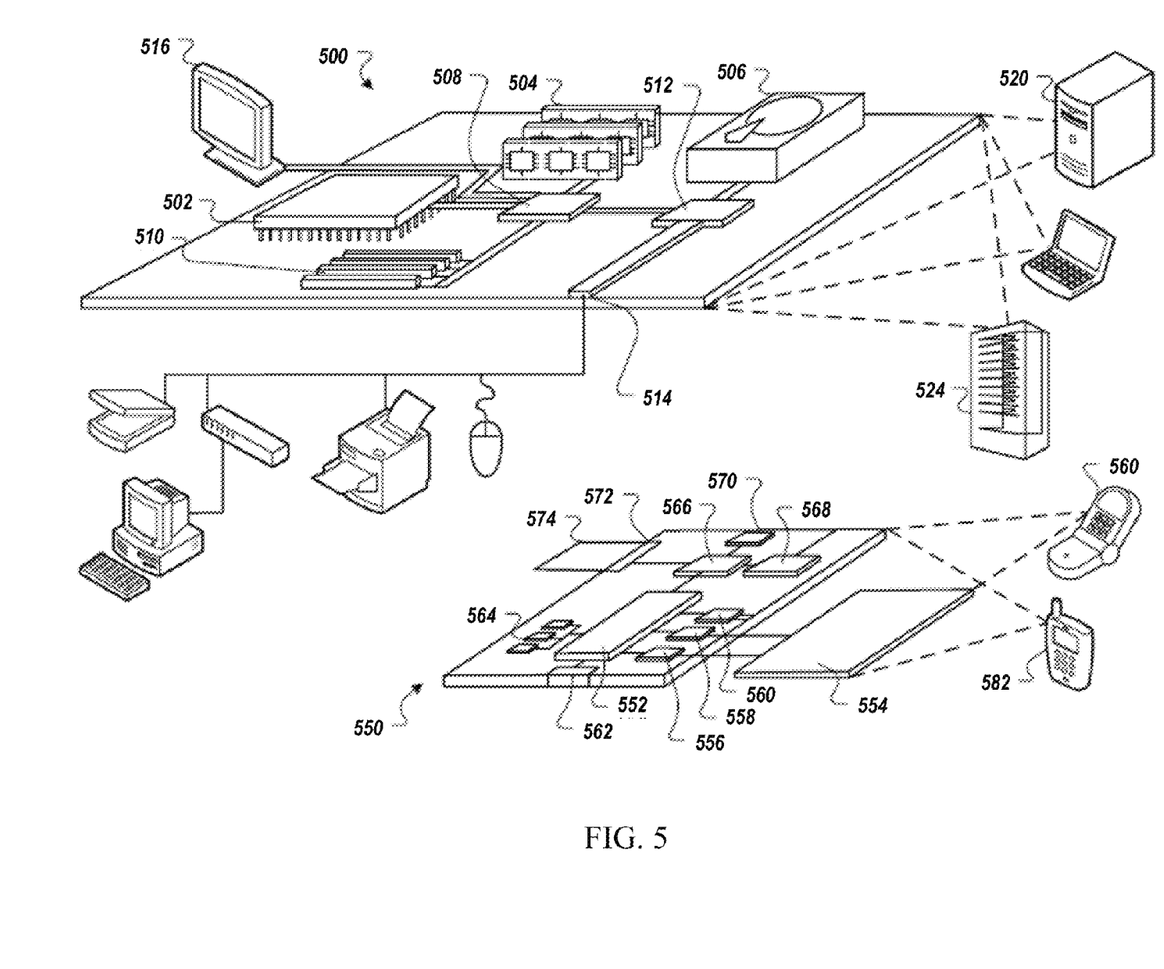
FIG. 5 is a block diagram of an example computing device and an example mobile computing device, for use in illustrative embodiments described herein.

FIG. 5 shows an example of a computing device 500 and a mobile computing device 550 that can be used in the methods and systems described herein. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provided as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A spectroscopic system for measuring chemical composition and/or trace impurities in a compressible fluid sample, the system comprising:
   an electromagnetic radiation source for generating electromagnetic radiation;
   optics for directing the generated electromagnetic radiation through a sample cell containing a compressible fluid sample;
   an optical detector array for receiving electromagnetic radiation from the sample cell containing the fluid sample and for generating an electrical signal indicative of spectral information associated with the fluid sample;
   a pressure modulating system for varying the pressure of the fluid sample in the sample cell, thereby varying sample density; and
   a processor and memory having instructions stored thereon, wherein the instructions, when executed by the processor, cause the processor to identify and/or analyze at least two absorption spectra obtained at different sample pressures in the fluid sample, thereby identifying a differential absorption spectrum for the fluid sample.

2. The spectroscopic system of claim 1 wherein the pressure modulating system comprises:
   a valve assembly having a first input port, a second input port, and an output port, the valve assembly being configured to selectably permit flow (i) between the first input port and the output port and (ii) between the second input port and the output port, according to a selectable configuration of the valve assembly; and
   a check valve connecting between the first input port and the second input port to allow setting of measurement pressure of the fluid sample in the sample cell.

3. The spectroscopic system of claim 2, wherein the valve assembly comprises a three-way valve.

4. The spectroscopic system of claim 1, wherein the sample cell is a flow cell permitting flow of the fluid sample therethrough during measurement.

5. The spectroscopic system of claim 1, wherein the pressure modulating system allows for setting measurement pressure of the fluid sample in the sample cell at a first pressure and at a second pressure while maintaining a consistent flow rate throughout measurement.

\* \* \* \* \*